United States Patent
Ashworth et al.

(10) Patent No.: US 7,074,781 B2
(45) Date of Patent: Jul. 11, 2006

(54) CONDENSED AZEPINES AS VASOPRESSIN AGONISTS

(75) Inventors: Doreen Mary Ashworth, Southampton (GB); Gary Robert William Pitt, Hampshire (GB); Peter Hudson, Copenhagen S (DK); Christopher Martyn Yea, Romsey (GB); Richard Jeremy Franklin, Wokingham (GB)

(73) Assignee: Ferring BV, Hoofddorp (NL)

( * ) Notice: Subject to any disclaimer, the term of this patent is extended or adjusted under 35 U.S.C. 154(b) by 414 days.

(21) Appl. No.: 10/130,749

(22) PCT Filed: Jan. 4, 2001

(86) PCT No.: PCT/GB01/00023

§ 371 (c)(1), (2), (4) Date: May 23, 2002

(87) PCT Pub. No.: WO01/49682

PCT Pub. Date: Jul. 12, 2001

(65) Prior Publication Data

US 2003/0087892 A1    May 8, 2003

(30) Foreign Application Priority Data

Jan. 5, 2000  (GB)  .................... 0000079

(51) Int. Cl.
- *A61P 13/00* (2006.01)
- *A61K 31/55* (2006.01)
- *C07D 403/12* (2006.01)
- *C07D 471/04* (2006.01)
- *C07D 495/04* (2006.01)

(52) U.S. Cl. ................. 514/213.01; 540/593
(58) Field of Classification Search ........... 514/213.01; 540/593
See application file for complete search history.

(56) References Cited

U.S. PATENT DOCUMENTS 5,753,644 A   5/1998   Ogawa et al.   ........... 514/213

FOREIGN PATENT DOCUMENTS

| EP | 0 514 667 A1 | 11/1992 |
|---|---|---|
| WO | WO 94/12476 A1 | 6/1994 |
| WO | WO 94/20473 A1 | 9/1994 |

OTHER PUBLICATIONS

Patent Abstracts of Japan vol. 1999, No. 08, Jun. 30, 1999 & JP 11 060488 A (Otuka Pharmaceutical Co., Ltd.), Mar. 2, 1999 (Abstract).

Patent Abstracts of Japan vol. 018, No. 140, Mar. 8, 1994 & JP 05 320135 A (Yamanouchi Pharmaceutical Co., Ltd.), Dec. 3, 1993 (Abstract).

*Primary Examiner*—Brenda Coleman
(74) *Attorney, Agent, or Firm*—Foley & Lardner LLP

(57) ABSTRACT

This invention provides novel compounds according to general formula (1) wherein A is a bicyclic or tricyclic azepine derivative, $V^1$ and $V^2$ are both H, OMe or F, or one of $V^1$ and $V^2$ is Br, Cl, F, OH, OMe, OBn, OPh, O-acyl, $N_3$, $NH_2$, NHBn or NH-acyl and the other is H, or $V^1$ and $V^2$ together are =O, —O(CH$_2$)$_p$O— or —S(CH$_2$)$_p$S—; $W^1$ is either O or S; $X^1$ and $X^2$ are both H, or together are =O or =S; Y is OR$^5$ or NR$^6$R$^7$; R$^1$, R$^2$, R$^3$ and R$_4$ are independently selected from H, lower alkyl, lower alkyloxy, F, Cl and Br; R$^5$ is selected from H and lower alkyl; R$^6$ and R$^7$ are independently selected from H and lower alkyl, or together are —(CH$_2$)$_n$—; n=3, 4, 5, 6; and p is 2 or 3. The compounds are agonists at the vasopressin V2 receptor and are useful as antidiuretics and procoagulants. The invention further comprises pharmaceutical compositions incorporating these vasopressin agonists, which compositions are particularly useful in the treatment of central diabetes insipidus, nocturnal enuresis and nocturia.

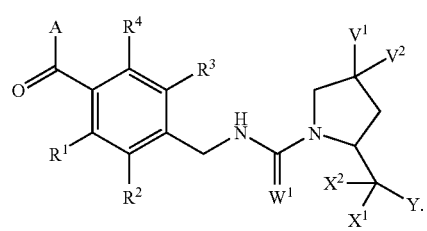

16 Claims, No Drawings

CONDENSED AZEPINES AS VASOPRESSIN AGONISTS

This application is a national stage entry under 35 U.S.C. § 371 of PCT/GB01/00023, filed Jan. 4, 2001.

FIELD OF INVENTION

The present invention relates to a class of novel chemical entities which act as agonists of the peptide hormone vasopressin. They reduce urine output from the kidneys and so are useful in the treatment of certain human diseases characterised by polyuria. They are also useful in the control of urinary incontinence and bleeding disorders.

BACKGROUND TO THE INVENTION

Vasopressin is a peptide hormone secreted by the posterior pituitary gland. It acts on the kidney to increase water retention and so reduce urine output. For this reason, vasopressin is alternatively known as "antidiuretic hormone". It also acts on the vasculature, where it produces a hypertensive effect. The cellular receptors that mediate these two actions have been characterised and shown to be different. The antidiuretic action is mediated by the type-2 vasopressin receptor, commonly called the $V_2$ receptor. Agents that can interact with the $V_2$ receptor and activate it in the same way as vasopressin are called $V_2$ receptor agonists (or simply $V_2$ agonists). Such agents will have an antidiuretic action. If these agents interact selectively with the $V_2$ receptor and not the other vasopressin receptor subtypes, then they will not have the hypertensive effect of vasopressin. This would be an important safety consideration and make such agents attractive for the treatment of human disease conditions characterised by polyuria (which is herein taken to mean excessive urine production).

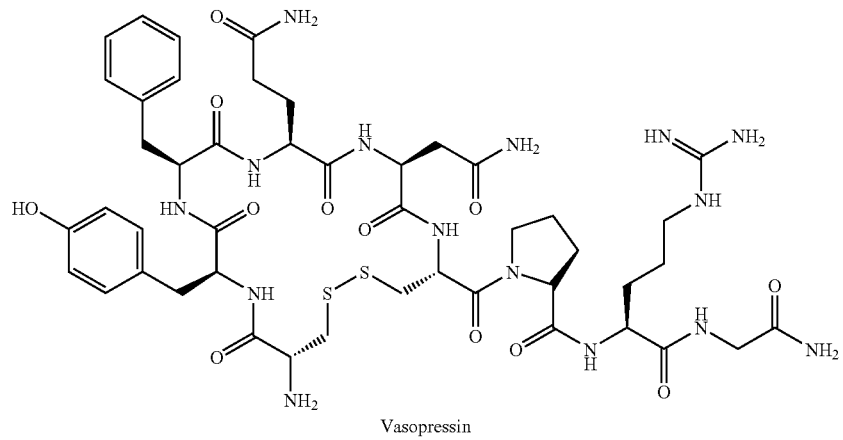

Vasopressin

In fact, such an agent is already in use in human therapy. Desmopressin (otherwise [1-desamino, D-Arg$^8$]vasopressin, Minirin™, DDAVP™) is a peptide analogue of vasopressin which is selectively an agonist at the $V_2$ receptor. It is used in the treatment of central diabetes insipidus, which is a condition that results from defective secretion of vasopressin. It is also employed in the control of nocturnal enuresis and may also be of use in the control of nocturia. However, desmopressin is not an ideal agent in all respects. Even the best current syntheses of the agent are lengthy, and desmopressin is not amenable to the most convenient of purificaton techniques such as crystallisation. Consequently, desmopressin is relatively expensive. It has a very low oral bioavailability, and there is some variability in this parameter.

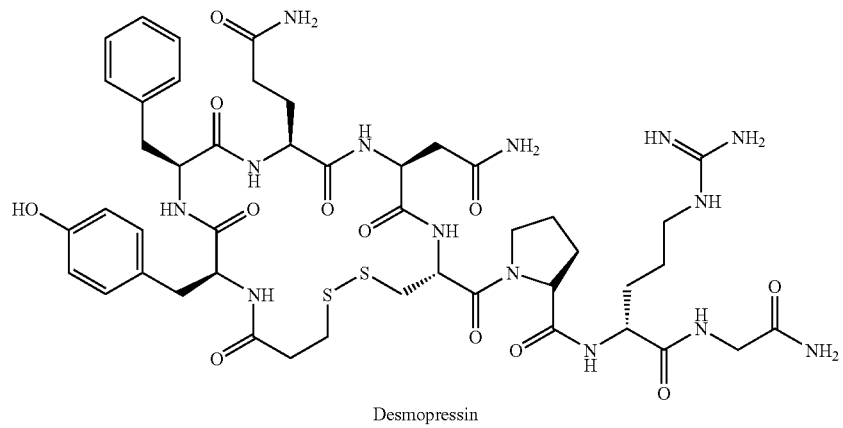

Desmopressin

Overall then, there exists a need for a selective vasopressin $V_2$ receptor agonist that is easy to prepare and purify, and that has a high and predictable oral bioavailability. Such properties are most likely to be obtained with a non-peptide compound. These considerations have led other groups to investigate non-peptide vasopressin $V_2$ agonists, and their results are disclosed in, for example, International Patent Applications WO97/22591, WO99/06403, WO99/06409, WO00/46224, WO00/46225, WO00/46227 and WO00/46228. The compounds disclosed in these documents are, however, less than ideal. In particular, they have poor oral bioavailability, probably due in part to their low aqueous solubility. The present invention provides compounds with improved solubility and bioavailability.

Besides its antidiuretic actions, desmopressin is used to increase the concentration in the blood of the coagulation proteins known as Factor VIII and von Willebrand factor. In the clinical context, this makes desmopressin useful in the treatment of haemophilia A and von Willebrand's disease. Similar applications would be open to the non-peptide agonists of the present invention.

SUMMARY OF THE INVENTION

As disclosed herein, the present invention relates to a series of compounds that are non-peptide agonists of vasopressin and which are selective for the $V_2$ receptor subtype. The compounds are described by general formula 1

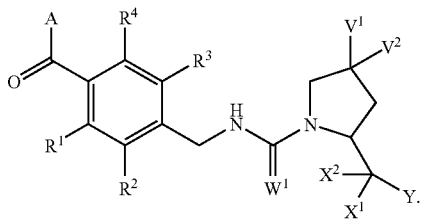

1 wherein:

A is a bicyclic or tricyclic azepine derivative selected from general formulae 2 to 7

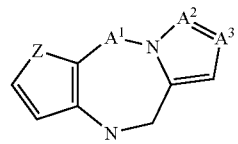

2

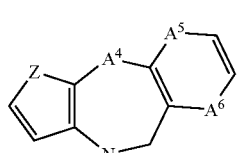

3

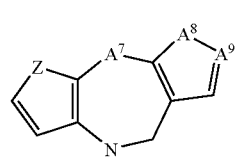

4

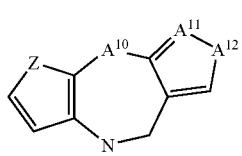

5

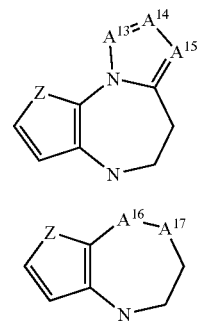

6

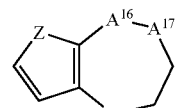

7

$A^1$, $A^4$, $A^7$ and $A^{10}$ are each independently selected from $CH_2$, O and $NR^8$;

$A^2$, $A^3$, $A^9$, $A^{11}$, $A^{13}$, $A^{14}$ and $A^{15}$ are each independently selected from CH and N;

either $A^5$ is a covalent bond and $A^6$ is S, or $A^5$ is N=CH and $A^6$ is a covalent bond;

$A^8$ and $A^{12}$ are each independently selected from NH and S;

$A^{16}$ and $A^{17}$ are both $CH_2$, or one of $A^{16}$ and $A^{17}$ is $CH_2$ and the other is selected from O, $SO_x$, and $NR^8$, $V^1$ and $V^2$ are both H, OMe or F, or one of $V^1$ and $V^2$ is Br, Cl, F, OH, OMe, OBn, OPh, O-acyl, $N_3$, $NH_2$, NHBn or NH-acyl and the other is H, or $V^1$ and $V^2$ together are =O, —O(CH$_2$)$_p$O— or —S(CH$_2$)$_p$S—;

$W^1$ is either O or S;

$X^1$ and $X^2$ are both H, or together are =O or =S;

Y is $OR^5$ or $NR^6R^7$;

Z is S or —CH=CH—;

$R^1$, $R^2$, $R^3$ and $R^4$ are independently selected from H, lower alkyl, lower alkyloxy, F, Cl and Br;

$R^5$ is selected from H and lower alkyl;

$R^6$ and $R^7$ are independently selected from H and lower alkyl, or together are —(CH$_2$)$_n$—;

$R^8$ is H or lower alkyl;

n=3, 4, 5 or 6;

p is 2 or 3; and x is 0, 1 or 2.

The invention further comprises pharmaceutical compositions incorporating these vasopressin agonists, which compositions are particularly useful in the treatment of central diabetes insipidus, nocturnal enuresis and nocturia.

DESCRIPTION OF THE INVENTION

The present invention comprises N-benzylcarbamyl pyrrolidine derivatives defined by general formula 1.

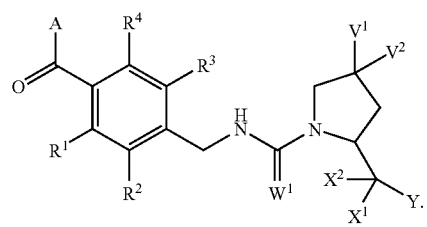

1

In this formula, A represents a bicyclic or tricyclic azepine group according to one of the general formulae 2–7.

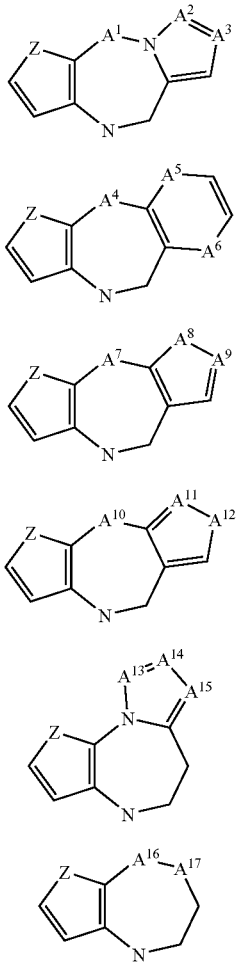

$A^1$, $A^4$, $A^7$ and $A^{10}$ represent divalent groups selected from methylene (—$CH_2$—), oxygen (—O—) and substituted nitrogen (—$NR^8$—). $A^2$, $A^3$, $A^9$, $A^{11}$, $A^{13}$, $A^{14}$ and $A^{15}$ represent either a nitrogen atom (—N=) or a methine group (—CH=). $A^5$ can represent a covalent bond, in which case $A^6$ represents a sulphur atom (—S—) such that the ring that includes these two groups is a thiophene ring. Alternatively, $A^5$ can represent a group —N=CH—, in which case $A^6$ represents a covalent bond such that the ring that includes these two groups is a pyridine ring. $A^8$ and $A^{12}$ represent either —NH— or a sulphur atom (—S—). $A^{16}$ and $A^{17}$ represent divalent groups. Both may be methylene groups (—$CH_2$—) or one is a methylene group and the other is selected from hydroxymethylene (—CH(OH)—), difluoromethylene (—$CF_2$—), oxygen (—O—), substituted nitrogen (—$NR^6$—) and sulphur or oxidised sulphur (—S—, —SO—, or —$SO_2$—).

$V^1$ and $V^2$ may both be hydrogen, methoxy or fluorine, or one may be selected from bromine, chlorine, fluorine, hydroxy, lower alkoxy, benzyloxy, phenoxy, acyloxy, azido, amino, benzylamino and acylamido (Br, Cl, F, OH, O-lower alkyl, OBn, OPh, O-acyl, $NH_2$, NHBn and NH-acyl) provided that the other is hydrogen, or $V^1$ and $V^2$ together may represent an oxygen atom such that the fragment $CV^1V^2$ is a carbonyl group (C=O). $V^1$ and $V^2$ may also be an ethylene- or propylene-dioxy or -dithio chain (—$O(CH_2)_2O$—, —$O(CH_2)_3O$—, —$S(CH_2)_2S$—, —$S(CH_2)_3S$—) such that $CV^1V^2$ is a 1,3-dioxolane, 1,3-dioxane, 1,3-dithiolane or 1,3 dithiane ring.

$W^1$ is either an oxygen or a sulphur atom.

$X^1$ and $X^2$ may either both be hydrogen, or together they may represent an oxygen or sulphur atom such that the fragment $CX^1X^2$ is a carbonyl or thiocarbonyl group (C=O or C=S).

Y is either a group —$OR^5$ or a group —$NR^6R^7$.

Z represents either a sulphur atom, such that the ring that includes it is a thiophene ring, or it represents a group —CH=CH—, such that the ring is a benzene ring.

$R^1$, $R^2$, $R^3$ and $R^4$ are each independently selected from hydrogen, lower alkyl groups, lower alkyloxy groups and the halogens fluorine, chlorine and bromine.

$R^5$ may be either a hydrogen atom or a lower alkyl group.

$R^6$ and $R^7$ may each independently be hydrogen atoms or lower alkyl groups, or together they may constitute a chain of between 3 and 6 methylene groups such that, together with the nitrogen atom to which they are attached, they form an azetidine, pyrrolidine, piperidine or perhydroazepine ring.

$R^8$ may be hydrogen or a lower alkyl group.

In the context of the present disclosure, the term "lower alkyl" is intended to include straight chain and branched alkyl groups and cycloalkyl groups of between 1 and 6 carbon atoms. For example, methyl, ethyl, isopropyl, tert-butyl, neopentyl and cyclohexyl are all within the scope of the term lower alkyl. The term "acyl" denotes lower alkyl carbonyl groups such as acetyl, pivaloyl, cyclopropylcarbonyl and the like. Formyl is also considered to be an acyl group.

Certain compounds of general formula 1 are capable of forming salts with acids or bases. For example, compounds containing one or more nitrogen atoms can form addition salts with mineral and organic acids such as hydrochloric acid, sulphuric acid, phosphoric acid, acetic acid, trifluoroacetic add, methanesulphonic acid, citric acid and benzoic acid. Compounds containing acidic groups can form salts with bases. Examples of such salts include the sodium, potassium, calcium, triethylammonium and tetraethylammonium salts. Furthermore, compounds that have both acidic and basic groups can form internal salts (zwiterions). Insofar as these salts are pharmaceutically acceptable, they are included within the scope of the invention.

The compounds according to general formula 1 all have at least one stereogenic centre (a tetrahedral carbon atom bearing four different substituents) and so can exist as optical isomers such as enantiomers and diastereomers. Such isomers, and mixtures thereof, are all intended to be within the scope of the present invention.

In a preferred embodiment of the present invention, A is a group according to general formula 2. In another preferred embodiment of the present invention, A is a group according to general formula 3. In another preferred embodiment of the present invention, A is a group according to general formula 4. In another preferred embodiment of the present invention, A is a group according to general formula 5. In another preferred embodiment of the present invention, A is a group according to general formula 6.

In another preferred embodiment of the present invention, A is a group according to general formula 7. In a more preferred embodiment, A is a tetrahydro-1-benzazepin-1-yl group, i.e. a group according to general formula 7 in which Z is —CH=CH— and both $A^{16}$ and $A^{17}$ are methylene groups.

In another preferred embodiment, one of $R^1$ and $R^2$ is chlorine or a methyl group and the other is hydrogen, with both $R^3$ and $R^4$ also being hydrogen.

In another preferred embodiment, one of $V^1$ and $V^2$ is a methoxy or benzyloxy group and the other is hydrogen.

In yet another preferred embodiment, $X^1$ and $X^2$ together represent an oxygen atom and Y is —$NR^6R^7$.

Particularly preferred embodiments of the present invention are those that combine two or more of the above preferred features.

A still more preferred embodiment of the present invention is a compound according to general formula 8.

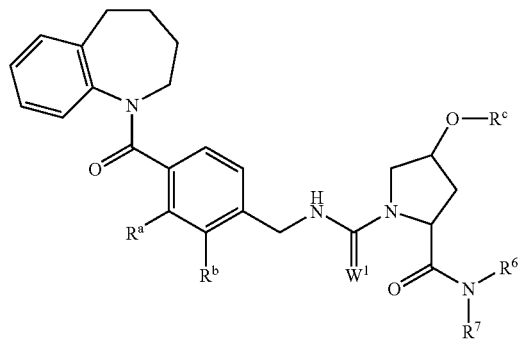

8

In general formula 8, $W^1$, $R^5$ and $R^6$ are as defined above for 1. One of $R^a$ and $R_b$ is hydrogen and the other is either chlorine or a methyl group. $R^c$ is either a methyl group or a benzyl group.

A yet more preferred embodiment is a compound of general formula 8A in which the stereochemistry is as shown.

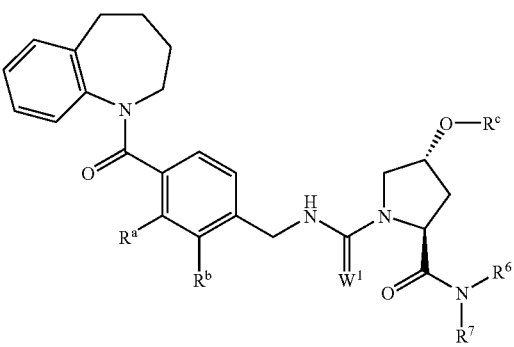

8A

Another preferred embodiment of the present invention is a compound according to general formula 1 in which $V^1$ and $V^2$ are both hydrogen. In a more preferred embodiment, $X^1$ and $X^2$ together are an oxygen atom and Y is $NR^6R^7$. More preferred still is a compound according to general formula 9.

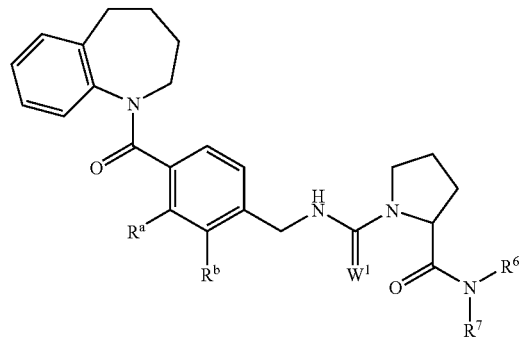

9

In general formula 9, $W^1$, $R^5$ and $R^6$ are as defined above for 1. One of $R^a$ and $R^b$ is hydrogen and the other is either chlorine or a methyl group.

Even more preferred is a compound according to general formula 9A in which the stereochemistry is as shown.

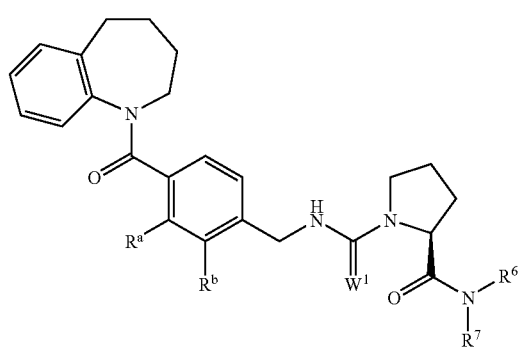

9A

Individual preferred compounds within the present invention include (but are not limited to) the following:

1-(2-methyl-4-(2,3,4,5-tetrahydro-1-benzazepin-1-ylcarbonyl)benzylcarbamoyl)-L-proline-N,N-dimethylamide, (4R)-4-hydroxy-1-(2-methyl-4-(2,3,4,5-tetrahydro-1-benzazepin-1-ylcarbonyl)benzylcarbamoyl)-L-proline-N,N-dimethylamide, (4R)-1-(3-chloro-4-(2,3,4,5-tetrahydro-1-benzazepin-1-ylcarbonyl)benzylcarbamoyl)-4-methoxy-L-proline-N,N-dimethylamide, (4R)-1-(2-chloro-4-(2,3,4,5-tetrahydro-1-benzazepin-1-ylcarbonyl)benzylcarbamoyl)-4-methoxy-L-proline-N,N-dimethylamide, (4R)-4-benzyloxy-1-(2-methyl-4-(2,3,4,5-tetrahydro-1-benzazepin-1-ylcarbonyl)benzylcarbamoyl)-L-proline-N,N-dimethylamide, (4R)-4-methoxy-1-(2-methyl-4-(2,3,4,5-tetrahydro-1-benzazepin-1-ylcarbonyl)benzylcarbamoyl)-L-proline-N,N-dimethylamide, (4R)-4-methoxy-1-(3-methyl-4-(2,3,4,5-tetrahydro-1-benzazepin-1-ylcarbonyl)benzylcarbamoyl)-L-proline-N,N-dimethylamide, (4R)-1-(2-chloro-4-(5,6,7,8-tetrahydro-4H-thieno[3,2-b]azepin-4-ylcarbonyl)benzylcarbamoyl)-4-methoxy-L-proline-N,N-dimethylamide, (4R)-1-(4-(10,11-dihydro-5H-pyrrolo[2,1-c](1,4)benzodiaz-epin-10-ylcarbonyl)-2-methyl-benzylcarbamoyl)-4-methoxy-L-proline-N,N-dimethylamide, (4R)-1-(2-chloro-4-(10,11-dihydro-5H-pyrrolo[2,1-c](1,4)benzodiazepin-10-ylcarbonyl)benzylcarbamoyl)-4-methoxy-L-proline-N,N-dimethylamide, and (4R)-1-(4-(10,11-dihydro-5H-pyrrolo[2,1-c](1,4)benzodiazepin-10-ylcarbonyl)-2-methyl-benzylcarbamoyl)-4-methoxy-L-proline-N,N-dimethylthioamide.

The compounds of the present invention can be prepared using methods generally known in the art. The compounds of general formula 1 can be considered to be composed of three linked fragments (A–C).

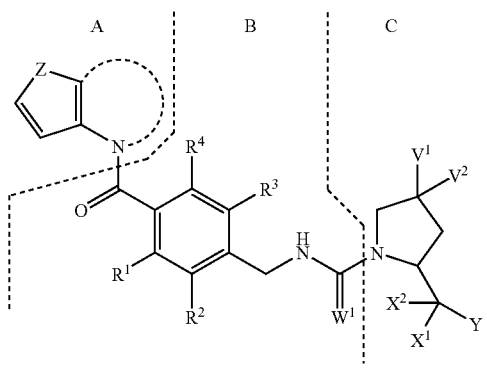

The three fragments will generally be prepared separately and then combined at a late stage in the synthesis. Some instances of the various groups ($R^1$–$R^4$, $V^1$, $V^2$, $X^1$, $X^2$ etc.) might be incompatible with this assembly and so will require the use of protecting groups. The use of protecting groups is well known in the art (see for example "Protective Groups in Organic Synthesis", T. W. Greene, Wiley-Interscience, 1981). Particular groups that may require protection are amines (protected as amides or carbamates), alcohols (protected as esters or ethers) and carboxylic acids (protected as esters). For the purposes of this discussion, it will be assumed that such protecting groups as are necessary are in place.

The fragments A, B and C can be combined according to two strategies to give the compounds of formula 1. In the first, fragments A and B are linked to give a fragment corresponding to AB, which is then combined with fragment C. In the second, fragments B and C are linked to give a fragment corresponding to BC, which is then combined with fragment A. The chemistry involved in the condensation of fragment A with B, and that involved in the condensation of fragment B with fragment C, will be the same whichever strategy is followed. We have found that the first strategy is more flexible when working on a small scale and for preparing a selection of compounds. Nevertheless, it is possible that the second strategy would be advantageous for the preparation of a selected compound on a large scale.

Formation of Fragment AB

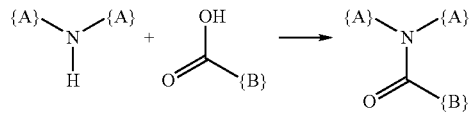

Here, {A} and {B} represent part structures of the fragments A and B respectively. The formation of amides by the condensation of carboxylic acids with amines is well known. In general, the acid and the amine are mixed in an aprotic solvent such as dichloromethane or dimethylformamide in the presence of a condensing agent such as a carbodiimide (for example "water-soluble carbodiimide", which is N-ethyl-N-(3-dimethylaminopropyl)-carbodiimide) or a reactive phosphorus derivative (for example "BOP", which is (benzotriazol-1-yloxy)tris(dimethylamino)phosphonium hexafluorophosphate). The reaction may optionally be catalysed by a tertiary amine such as triethylamine or 4-dimethylaminopyridine. Alternatively, the carboxylic acid may be converted to a more reactive derivative such as the acid chloride. Such a derivative can then be reacted with the amine as described above but without the need for a condensing agent.

Formation of Fragment BC

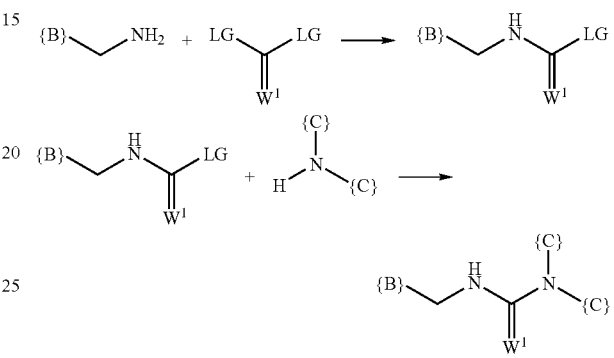

Formation of the urea or thiourea bond between fragments B and C can be most easily achieved by allowing the primary amine corresponding to fragment B to react with a derivative of carbonic acid such as phogene (wherein LG above is chlorine) or carbonyidiimidazole (wherein LG is 1-imidazolyl) to form an intermediate carbamic acid derivative. When $W^1$ is sulphur rather than oxygen, thiophosgene or thiocarbonyldiimidazole is used. The reaction is conveniently carried out in an aprotic solvent such as dichloromethane or dimethylformamide in the presence of a tertiary amine such as triethylamine or N,N-diisopropylethylamine. After allowing sufficient time for the formation of the intermediate, the secondary amine corresponding to fragment C can be added to the reaction mixture. It is not necessary to isolate the intermediate carbamate derivative.

As a variation of this process, it is possible to reverse the order of addition of the amines corresponding to fragments B and C, such that the carbamate derivative is formed from the secondary amine, and the primary amine is added subsequently.

Overall then, the following intermediates are required for the synthesis of the compounds of the present invention i) For Fragment A

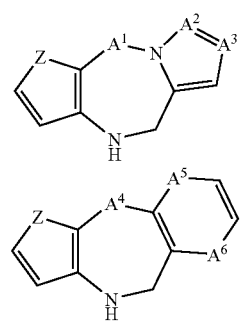

-continued

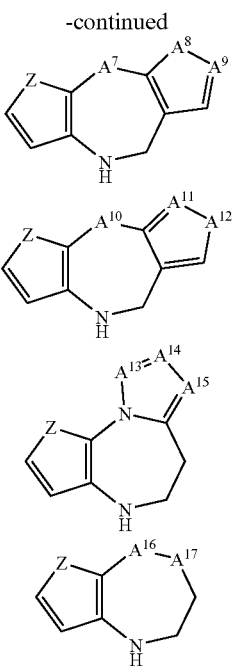

Fused azepines according to these general formulae can be prepared according to methods reported in the literature. See for example: Aranapakam et al., Bioorg. Med. Chem. Lett. 1993, 1733; Artico et al., Farmaco. Ed. Sci. 24, 1969, 276; Artico et al., Farmaco. Ed. Sci. 32, 1977, 339; Chakrabarti et al., J. Med. Chem. 23, 1980, 878; Chakrabarti at al., J. Med. Chem. 23, 1980, 884; Chakrabarti et al., J. Med. Chem. 32, 1989, 2573; Chimirri et al., Heterocycles 36, 1993, 601; Grunewald et al., J. Med. Chem. 39, 1996, 3539; Klunder et al., J. Med. Chem. 35, 1992, 1887; Liegéois et al., J. Med. Chem. 37, 1994, 519; Olagbemiro et al., J. Het. Chem. 19, 1982, 1501; Wright et al., J. Med. Chem. 23, 1980, 462; Yamamoto et al., Tet. Lett. 24, 1983, 4711; and International patent application, publication number WO99/06403.

Some of them are Items of commerce.

ii) For Fragment B

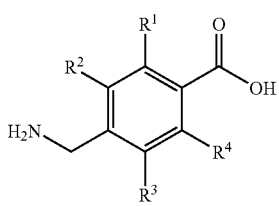

Because the primary amine and the carboxylic acid groups are incompatible, they must be developed separately and protected. Substituted benzoic acids are well known, and the carboxylic acid is conveniently protected as its methyl ester. The primary amine can be elaborated from the corresponding nitrile (by reduction) or the alcohol (by displacement with a nitrogen nucleophile). The best method will depend on the nature of the substituents $R^1$–$R^4$.

iii) For Fragment C

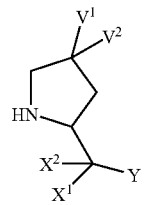

Pyrrolidine derivatives of this type are prepared according to the methods described in the literature. See for example: Dugave et al., Tet. Lett. 39, 1998, 1169; Petrillo et al., J. Med. Chem. 31, 1988, 1148; and Smith et al., J. Med. Chem. 31, 1988, 875.

Proline and hydroxyproline derivatives of defined stereochemistry are items of commerce and as such are convenient starting materials.

The present invention further comprises pharmaceutical compositions that include at least one compound according to the foregoing description as an active constituent. The composition may also include a second pharmacological agent such as a spasmolytic or a potassium channel blocker, these agents being known in the art to ameliorate bladder dysfunction. Preferably, the composition includes only one active constituent. The composition will include excipients selected from binding agents, bulking agents, dispersants, solvents, stabilising agents and the like, such excipients being generally known in the art.

The excipients used will depend on the intended nature of the formulation, which will, in turn, depend on the intended route of administration. Administration may be oral, transmucosal (such as sublingual, buccal, intranasal, vaginal and rectal), transdermal or by injection (such as subcutaneous, intramuscular and intravenous). Oral administration is generally preferred. For oral administration, the formulation will be a tablet or capsule. Other formulations include dry powders, solutions, suspensions, suppositories and the like.

In a further aspect, the present invention is a method of treating or controlling certain human physiological dysfunctions. This method comprises the administration to the person in need of such treatment of an effective amount of a pharmaceutical composition, which composition contains a compound according to the foregoing description as an active constituent. The compounds act to reduce urine output, and so the method of the invention can be applied to all conditions in which elevated urine output is a contributory factor. The compounds also increase the production of the blood coagulation proteins known as Factor VIII and von Willebrand factor, and so the treatment of bleeding disorders can be undertaken.

In a preferred embodiment, the condition treated is diabetes insipidus. This is a condition caused by an inability of the body to produce and secrete physiologically active vasopressin, with the result that water re-uptake is greatly reduced and large volumes of urine are produced.

In another preferred embodiment, the condition treated is nocturnal enuresis. This is defined as bladder emptying while the individual is sleeping. It is a condition that mainly affects children and a number of factors may be involved in its etiology.

In another preferred embodiment, the condition treated is nocturia. This is defined as production of sufficient urine during the night to require the individual to wake and empty his (or her) bladder. Again, this condition may be the result of a number of factors.

In another preferred embodiment, the condition treated is incontinence. This condition is characterised, in part, by reduced bladder capacity and control such that involuntary urination occurs unless the bladder is emptied frequently. Incontinence has been divided into two conditions, stress incontinence and urge incontinence. A number of etiological factors are thought to be involved. Treatment according to the invention is particularly useful for delaying the need for bladder emptying ("voiding postponement") in order to allow the incontinent subject a dry period of a few hours (such as up to four hours). Such voiding postponement may also be useful for the non-incontinent population, for example for people obliged to remain in meetings for extended periods.

In another preferred embodiment, the condition treated is haemophilia A or von Willebrand's disease. These are conditions in which Factor VIII or von Willebrand factor production is reduced and the individual suffers from prolonged bleeding.

In another preferred embodiment, the composition is administered prior to surgery (including dental surgery) to increase the coagulability of the blood and so reduce perioperative blood loss.

The administration of the compositions of the present invention will generally be under the control of a physician. The physician will determine the amount of composition to be administered and the dosing schedule, taking into account the patient's physical condition and the therapeutic goals. For an adult diabetes insipidus patient, a typical dose might be between 50 mg and 1 g of the active compound per day, taken as a single tablet or as up to four tablets throughout the day. For routes of administration other than the oral route, the amount of compound will be reduced, since non-oral routes tend to be more efficient in terms of delivering therapeutic agents into the systemic circulation. For the treatment of haemophilia A and von Willebrand's disease the amount of compound may need to be higher than for the treatment of diabetes insipidus.

The foregoing general description will now be further illustrated with a number of non-limiting examples.

EXAMPLES

Abbreviations

The following abbreviations have been used.

| Ac | Acetyl |
|---|---|
| AIBN | Azo-bis-(isobutyronitrile) |
| Bn | Benzyl |
| BOC | tert-Butyloxycarbonyl |
| (BOC)$_2$O | Di-tert-butyl dicarbonate |
| DMF | Dimethylformamide |
| Et | Ethyl |
| EtOAc | Ethyl acetate |
| IPA | Isopropanol |
| iPr | Isopropyl |
| M.S. | Mass spectrometry |
| Me | Methyl |
| NBS | N-Bromosuccinimide |
| pet. ether | petroleum ether, fraction boiling at 60–80° C. |
| Ph | Phenyl |
| tBu | tert-Butyl |
| THF | Tetrahydrofuran |
| WSCDI | Water-soluble carbodiimide |

Preparation of Intermediates

Reagents corresponding to fragment A and C were commercially available or prepared according to the published procedures except where detailed in the specific Examples. Reagents corresponding to fragment B were prepared as detailed below.

Example A 4-(tert-Butyloxycarbonylaminomethyl)-3-chlorobenzoic acid

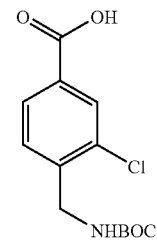

A1. Methyl 4-bromomethyl-3-chlorobenzoate

To a solution of methyl 3-chloro-4-methylbenzoate (5.0 g, 27.1 mmol) in carbon tetrachloride (50 ml) were added NBS (5.8 g, 32.0 mmol) and AIBN (0.442 g, 2.70 mmol). The mixture was stirred at reflux for 18 h. The mixture was allowed to cool to room temperature and then concentrated in vacuo. The residue was purified by flash chromatography on silica (eluant EtOAc:pet. ether 0:100 to 5:95); yield 5.96 g (84%).

A2. 4-(tert-Butyloxycarbonylaminomethyl)-3-chlorobenzoic acid

To a saturated solution of ammonia in ethanol (170 ml) was added methyl 4-bromomethyl-3-chlorobenzoate from Example A1 (5.5 g, 20.9 mmol). The mixture was stirred at room temperature for 1 h and then concentrated in vacuo. The residue was triturated with diethyl ether and the resultant white crystals were filtered off and washed with more diethyl ether. To a solution of this solid in water (100 ml) were added solutions of (BOC)$_2$O (5.0 g, 23.0 mmol) in dioxan (100 ml) and sodium hydroxide (1.86 g, 46.0 mmol) in water (100 ml). The mixture was stirred at room temperature for 18 h and then concentrated in vacuo. The aqueous residue was acidified with citric acid and extracted with chloroform/IPA. The organic layer was washed with water, dried over MgSO$_4$, and concentrated in vacuo to give a white solid; yield 2.89 (67%).

Example B

4-Cyano-3-methylbenzoic acid

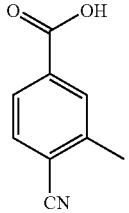

To a solution of 4-bromo-2-methylbenzonitrile (2.0 g, 10.2 mmol) in THF (100 ml) at −78° C. under a nitrogen atmosphere was added dropwise a 2.5M solution of n-butyl lithium (4.48 ml, 11.2 mmol). The mixture was stirred at −78° C. for 1 h and then poured onto solid carbon dioxide (5 g) in THF (50 ml). The mixture was allowed to warm to room temperature. Water was added (200 ml) and the mixture was extracted with diethyl ether (3 times). The aqueous layer was acidified by addition of concentrated HCl and extracted with chloroform (3 times). The combined chloroform extracts were washed with water, dried over MgSO$_4$, and concentrated in vacuo to give a white solid; yield 1.2 g (73%).

Example C

4-Cyano-2-methylbenzoic acid

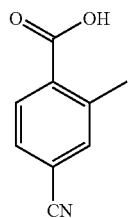

4-Bromo-3-methylbenzonitrile (2.0 g, 10.2 mmol) was reacted following the method of Example B to give a yellow solid which was triturated with hexane and filtered off; yield 0.96 g (59%).

Reagents corresponding to fragments A, B and C were combined to give the specific Examples as detailed below.

Example 1

1-(2-Methyl-4-(2,3,4,5-tetrahydro-1-benzazepin-1-ylcarbonyl)benzylcarbamoyl)-L-Proline-N,N-dimethylamide

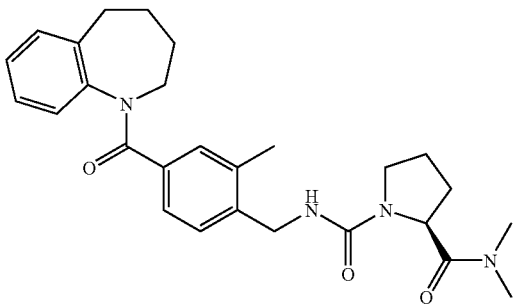

1A. 2-Methyl-4-((2,3,4,5-tetrahydro-1H-benzo[b]azepine)-1-carbonyl)-benzonitrile To a solution of 2,3,4,5-tetrahydro-1H-benzo[b]azepine (0.80 g, 5.44 mmol) in dichloromethane (50 ml) were added 4-cyano-3-methylbenzoic acid (0.96 g, 5.95 mmol), triethylamine (0.60 g, 5.95 mmol), 4-(dimethylamino)pyridine (0.73 g, 5.95 mmol) and WSCDI (1.24 g, 6.48 mmol). The mixture was stirred at reflux for 18 h, cooled and evaporated in vacua. The residue was partitioned between EtOAc and 1M KHSO$_4$. The organic layer was washed with saturated sodium bicarbonate solution and brine, dried over MgSO$_4$, and concentrated in vacuo. The crude material was purified by flash chromatography on silica (eluant EtOAc:pet. ether 30:70); yield 1.10 g (70%).

1B. 1-(4-(Aminomethyl)-3-methylbenzoyl)-2,3,4,5-tetrahydro-1H-benzo[b]azepine hydrochloride To a degassed solution of the cyanobenzazepine of Example 1A (1.10 g, 3.79 mmol) in methanol (50 ml) were added concentrated hydrochloric acid (0.98 ml, 11.3 mmol) and 10% palladium on carbon (0.80 g). Hydrogen gas was bubbled through the mixture for 5 h at room temperature. The catalyst was removed by filtering through a pad of celite and the filtrate was evaporated; yield 1.23 g (98%).

1C. 1-(2-Methyl-4-(2,3,4,5-tetrahydro-1-benzazepin-1-ylcarbonyl)benzylcarbamoyl-L-proline-N,N-dimethylamide To a solution of the amine of Example 1B (0.10 g, 0.302 mmol) in DMF (10 ml), under a nitrogen atmosphere, were added N,N-diisopropylethylamine (43 mg, 0.332 mmol) and carbonyl diimidazole (0.074 g, 0.453 mmol). The mixture was stirred at room temperature for 40 minutes. A solution of proline-N,N-dimethylamide (0.107 g, 0.756 mmol) in DMF (1 ml) was added. The mixture was stirred at room temperature for a further 16 hr. The solvent was removed in vacuo and the crude material was purified by flash chromatography on silica (eluant methanol:dichloromethane 5:95); yield 0.115 g (82%).

$^1$H NMR (CDCl$_3$): δ 1.35–1.55 (1H, m), 1.74–2.10 (3H, m), 2.11 (3H, s), 2.17–2.35 (1H, m), 2.60–2.82 (2H, m), 2.86 (3H, s), 2.90–3.14 (2H, m), 3.05 (3H, s), 3.26 (1H, dd, J=14.9 & 7.2 Hz), 3.40–3.53 (1H, m), 3.64–3.84 (1H, m), 4.03–4.19 (1H, m), 4.29–4.42 (1H, m), 4.55–4.68 (1H, m), 4.74–4.81 (1H, m), 4.85–4.98 (1H, m), 6.58 (1H, d, J=7.7 Hz), 6.75–6.89 (2H, m), 6.91–7.06 (3H, m), 7.16 (1H, d, J=6.5 Hz), 7.93–8.03 (1H, m) ppm.

M.S.: calc m/e=462.26; found [M+H]$^+$=463.2.

Example 2

(4R)-4-Hydroxy-1-(2-methyl-4-(2,3,4,5-tetrahydro-1-benzazepin-1-ylcarbonyl)benzylcarbamoyl)-L-proline-N,N-dimethylamide

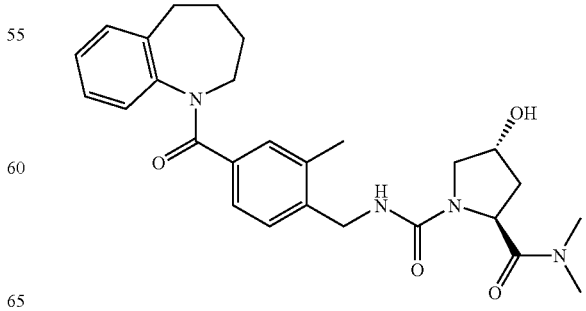

2A. L-trans-4-Hydroxyproline-N,N-dimethylamide hydrochloride

To a solution of BOC-hydroxyproline (2.99 g, 13.89 mmol) in dichloromethane (100 ml) were added N,N-diisopropylethylamine (3.7 ml, 21.24 mmol), 4-(dimethylamino)pyridine (1.74 g, 14.24 mmol), dimethylamine hydrochloride (1.72 g, 21.09 mmol) and WSCDI (3.17 g, 16.68 mmol). The mixture was stirred at room temperature for 30 hr. The mixture was diluted with dichloromethane (100 ml) and washed with 0.3M $KHSO_4$, saturated sodium bicarbonate solution and brine, dried over $MgSO_4$, and concentrated in vacuo to give a colourless gum. This crude material was taken up in 4N HCl/dioxan (50 ml) and stirred at room temperature for 1 hr and then concentrated in vacua. The residue was azeotroped with toluene and diethyl ether to give a white solid; yield 0.45 g (17%).

2B. (4R)-4-Hydroxy-1-(2-methyl-4-(2,3,4,5-tetrahydro-1-benzazepin-1-ylcarbonyl)benzylcarbamoyl)-L-proline-N,N-dimethylamide The amine of Example 1B (0.10 g, 0.302 mmol) was reacted with the amine of Example 2A (0.153 mg, 0.785 mmol) following the method of Example 1C. The product was purified by flash chromatography on silica (eluant chloroform:methanol:acetic acid 95:4:1); yield 0.95 g (66%).

$^1$H NMR ($CDCl_3$): δ 1.65–1.80 (2H, m), 1.85–2.00 (3H, m), 2.05–2.25 (1H, m), 2.10 (3H, s), 2.80–3.10 (3H, m), 2.85 (3H, s), 3.00 (3H, s), 3.40–3.30 (1H, m), 3.45–3.55 (1H, m), 3.65–3.95 (1H, m), 4.00–4.10 (1H, m), 4.30–4.55 (1H, m), 4.91 (1H, t, J=7.7 Hz), 5.15–5.30 (1H, m), 6.10–6.20 (1H, m), 6.55–6.65 (1H, m), 6.85–7.50 (5H, m) ppm.

M.S.: calc m/e=478.26; found $[M+H]^+$=479.2.

Examples 3–116

The additional examples set out in the following Tables were prepared using analogous methods.

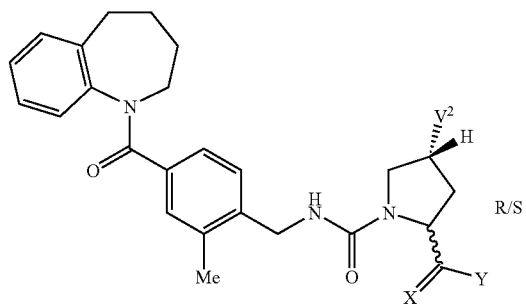

| Example No | R/S | $V^2$ | X | Y | $[M + H]^+$ |
|---|---|---|---|---|---|
| 3 | S | H | $H_2$ | OMe | 436.4 |
| 4 | R | H | $H_2$ | OMe | 436.2 |
| 5 | R/S | OPh | O | OH | 528.3 |
| 6 | R/S | OPh | O | $NMe_2$ | 555.3 |

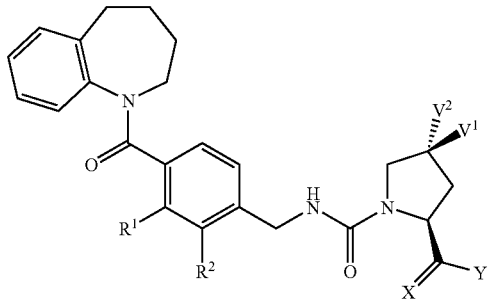

| Example No | $R^1$ | $R^2$ | $V^1$ | $V^2$ | X | Y | $[M + H]^+$ |
|---|---|---|---|---|---|---|---|
| 7 | H | Me | H | H | O | OtBu | 492.5 |
| 8 | H | Me | H | H | O | OH | 436.3 |
| 9 | H | Me | H | OH | O | OMe | 466.0 |
| 10 | H | Me | H | OAc | O | $NMe_2$ | 521.0 |
| 11 | H | Me |  | =O | O | $NMe_2$ | 477.3 |
| 12 | H | Me | H | OH | O | OEt | 480.2 |
| 13 | H | Me | H | $OCOcC_3H_5$ | O | $NMe_2$ | 547.3 |
| 14 | H | Me | H | OMe | O | $NMe_2$ | 493.5 |
| 15 | H | Cl | H | H | O | $NMe_2$ | 483.4 |
| 16 | H | Me | H | H | S | $NMe_2$ | 479.2 |
| 17 | H | Me | H | H | O | NMeEt | 477.2 |
| 18 | H | OMe | H | H | O | $NMe_2$ | 479.2 |
| 19 | H | Me | H | OMe | O | OMe | 480.2 |
| 20 | H | Me | H | H | O | OiPr | 478.2 |

-continued

| | | | | | | | |
|---|---|---|---|---|---|---|---|
| 21 | H | Me | H | OH | O | OH | 452.1 |
| 22 | H | Me | H | OBn | O | OiPr | 584.2 |
| 23 | H | Me | H | OH | O | OiPr | 494.1 |
| 24 | H | Me | H | OBn | O | NMe₂ | 569.2 |
| 25 | Me | H | H | H | O | NMe₂ | 463.2 |
| 26 | H | Me | H | OMe | O | OH | 466.2 |
| 27 | Cl | H | H | H | O | NMe₂ | 483.1 |
| 28 | H | Et | H | H | O | NMe₂ | 477.3 |
| 29 | H | Cl | H | H | S | NMe₂ | 499.2 |
| 30 | H | Cl | H | OBn | O | NMe₂ | 589.2 |
| 31 | H | Cl | H | OH | O | NMe₂ | 499.2 |
| 32 | H | Me | H | OEt | O | NMe₂ | 507.3 |
| 33 | H | Me | Br | H | O | NMe₂ | 541.1 |
| 34 | H | Me | H | Cl | O | OMe | 484.1 |
| 35 | H | Me | F | F | O | NMe₂ | 499.2 |
| 36 | H | Me | H | Cl | O | OH | 470.1 |
| 37 | H | Me | H | N₃ | O | NMe₂ | 504.3 |
| 38 | H | Me | H | Cl | O | NMe₂ | 497.2 |
| 39 | H | Me | H | OtBu | O | NMe₂ | 535.3 |
| 40 | H | Me | Cl | H | O | NMe₂ | 497.2 |
| 41 | H | Me | H | OPh | O | OMe | 542.3 |
| 42 | H | Me | H | F | O | OMe | 468.3 |
| 43 | H | Me | H | F | O | OH | 454.4 |
| 44 | H | Me | H | F | O | NMe₂ | 481.3 |
| 45 | H | Me | H | NHBn | O | NMe₂ | 568.0 |
| 46 | H | Me | OMe | OMe | O | OMe | 510.3 |
| 47 | H | Me | OMe | OMe | O | OH | 496.2 |
| 48 | H | Me | OMe | OMe | O | NMe₂ | 523.3 |

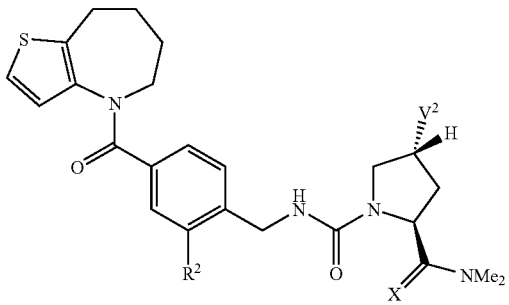

| Example No | R² | V² | X | [M + H]⁺ |
|---|---|---|---|---|
| 49 | Cl | H | O | 489.1 |
| 50 | Me | H | O | 469.2 |
| 51 | Me | OH | O | 485.0 |
| 52 | Cl | OMe | O | 519.3 |
| 53 | Me | OMe | O | 499.3 |
| 54 | Cl | OMe | S | 535.1 |

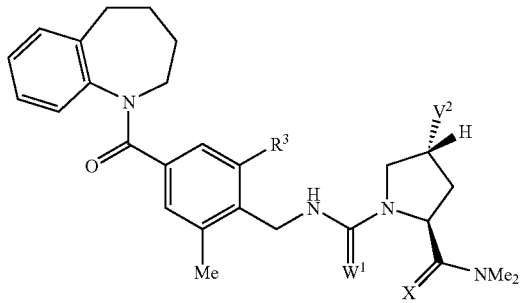

| Example No | R³ | V² | W¹ | X | [M + H]⁺ |
|---|---|---|---|---|---|
| 55 | H | H | S | O | 479.4 |
| 56 | H | OH | S | O | 495.0 |
| 57 | H | H | S | S | 495.1 |
| 58 | Me | H | O | O | 477.2 |
| 59 | H | OBn | S | O | 585.2 |
| 60 | H | OBn | O | S | 585.0 |

-continued
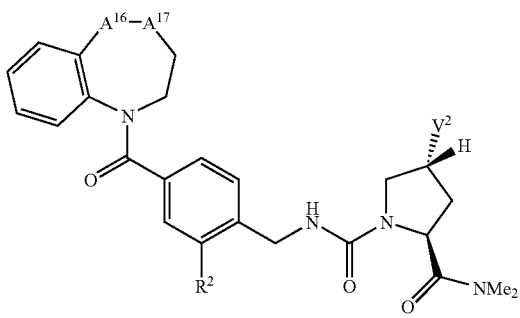
| Example No | A¹⁶ | A¹⁷ | R² | V² | [M + H]⁺ |
|---|---|---|---|---|---|
| 61 | NEt | CH$_2$ | Me | OMe | 522.4 |
| 62 | NH | CH$_2$ | Me | OMe | 494.3 |
| 63 | CH$_2$ | NiPr | Me | OMe | 536.4 |
| 64 | CH$_2$ | NH | Me | OMe | 494.5 |
| 65 | O | CH$_2$ | Cl | OMe | 515.2 |
| 66 | CH(OH) | CH$_2$ | Me | H | 479.2 |
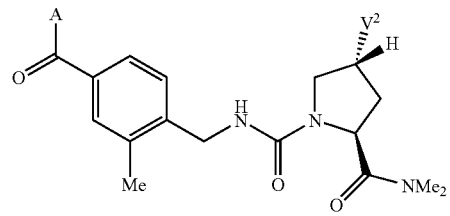
| Example No | A | V² | [M + H]⁺ |
|---|---|---|---|
| 67 | 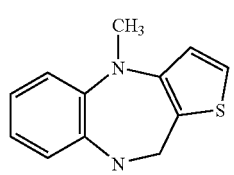 | H | 518.0 |
| 68 | 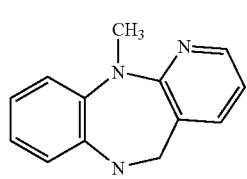 | H | 532.2 |
| 69 | 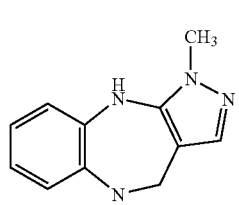 | H | 527.0 |
| 70 | 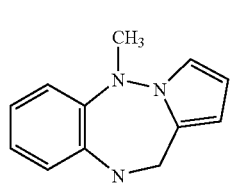 | H | 516.1 |
| 71 | | H | 515.0 |

-continued

| | | | |
|---|---|---|---|
| 72 | [benzoxazepine-pyridine structure] | H | 514.6 |
| 73 | [benzodiazepine-pyridine structure] | H | 513.7 |
| 74 | [benzodiazepine-triazole structure] | H | 502.1 |
| 75 | [benzodiazepine-pyrrole structure] | H | 500.7 |
| 76 | [N-CH₃ benzodiazepine-thiophene structure] | OH | 547.9 |
| 77 | [benzodiazepine-pyrazole structure] | OH | 517.6 |
| 78 | [di-N-CH₃ benzodiazepine-pyrazole structure] | OH | 546.3 |
| 79 | [benzodiazepine-thiophene structure] | H | 517.2 |
| 80 | [benzodiazepine-pyridine structure] | OBn | 619.2 |
| 81 | [benzodiazepine-pyridine structure] | OMe | 543.4 |

| | | | |
|---|---|---|---|
| 82 | 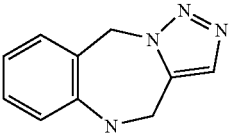 | OMe | 544.3 |
| 83 | 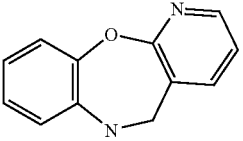 | OMe | 549.2 |
| 84 | 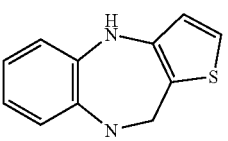 | OMe | 548.2 |
| 85 | 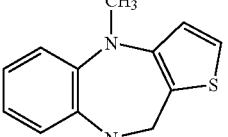 | OMe | 562.1 |
| 86 | 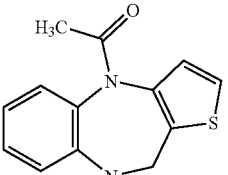 | OMe | 590.2 |
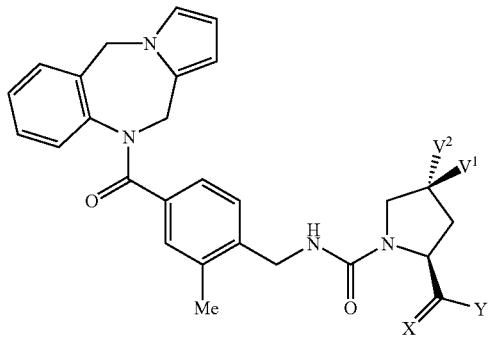
| Example No | $V^1$ | $V^2$ | X | Y | $[M + H]^+$ |
|---|---|---|---|---|---|
| 87 | H | H | S | $NMe_2$ | 516.2 |
| 88 | H | OBn | O | $NMe_2$ | 606.3 |
| 89 | H | OH | O | $NMe_2$ | 507.3 |
| 90 | H | OMe | O | $NMe_2$ | 530.3 |
| 91 | —OCH$_2$CH$_2$O— | | O | OMe | 545.3 |
| 92 | OMe | OMe | O | OMe | 547.3 |
| 93 | —OCH$_2$CH$_2$O— | | O | $NMe_2$ | 558.3 |
| 94 | —SCH$_2$CH$_2$S— | | O | $NMe_2$ | 590.2 |

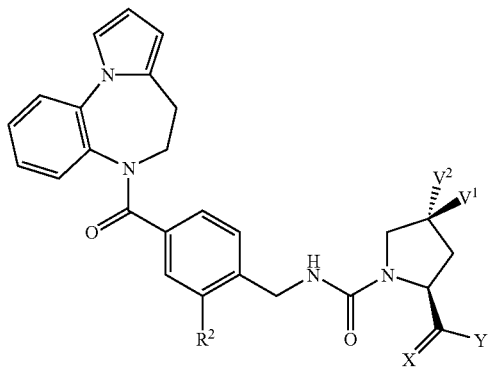

| Example No | R² | V¹ | V² | X | Y | [M + H]⁺ |
|---|---|---|---|---|---|---|
| 95 | Me | H | OH | O | NMe₂ | 516.1 |
| 96 | Me | H | H | S | NMe₂ | 516.2 |
| 97 | Me | H | OMe | O | NMe₂ | 530.4 |
| 98 | Me | —OCH₂CH₂O— | | O | OMe | 545.3 |
| 99 | Me | —OCH₂CH₂O— | | O | OH | 531.3 |
| 100 | Me | —OCH₂CH₂O— | | O | NMe₂ | 558.3 |
| 101 | Cl | H | H | O | NMe₂ | 551.5 |
| 102 | Me | H | OMe | O | NEt₂ | 558.3 |
| 103 | Me | H | OMe | O | piperidinyl | 570.3 |
| 104 | Me | H | OMe | S | NMe₂ | 546.2 |

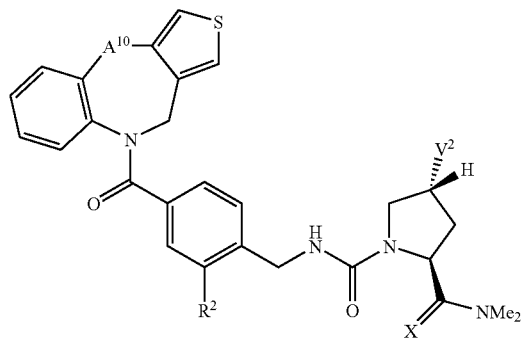

| Example No | A¹⁰ | R² | V² | X | [M + H]⁺ |
|---|---|---|---|---|---|
| 105 | O | Me | H | O | 519.3 |
| 106 | NMe | Me | H | O | 532.3 |
| 107 | NMe | Me | OH | O | 548.1 |
| 108 | NMe | Me | OBn | O | 638.2 |
| 109 | NMe | Me | OMe | O | 562.3 |
| 110 | O | Me | OMe | O | 549.2 |
| 111 | NMe | Me | Cl | O | 566.2 |
| 112 | NMe | Me | OMe | S | 578.2 |
| 113 | O | Cl | OMe | O | 569.1 |
| 114 | O | Me | OMe | S | 565.2 |
| 115 | O | Cl | OMe | S | 585.1 |
| 116 | NH | Me | OMe | O | 548.2 |

Example 117

In Vitro Biological Characterisation

The compounds of the invention are selective agonists at the $V_2$ receptor. In standard radio-ligand displacement assays, the compounds all give $K_i$ values below 10 μM for the $V_2$ receptor.

Example 118

In Vivo Biological Characterisation

The Brattleboro rat is recognised model for vasopressin deficiency (for a review see FD Grant, "Genetic models of vasopressin deficiency", *Exp. Physiol.* 85, 203S–209S, 2000). The animals do not secrete vasopressin and consequently produce large volumes of dilute urine. Compunds of the invention were administered to Brattleboro rats (0.1–10 mg/kg p.o. in methylcellulose. Urine was collected hourly and volumes were compared with control animals. Animals had free access to food and water throughout the experiment. Representative results are given in the Table. Results for Desmopressin are given for comparison.

| Compound of Example | Dose | % inhibition of urine output (at 1 hour) |
|---|---|---|
| 1 | 1 mg/kg | 82 |
| 14 | 1 mg/kg | 84 |
| 52 | 1 mg/kg | 90 |
| 54 | 1 mg/kg | 68 |
| 85 | 1 mg/kg | 63 |
| 90 | 1 mg/kg | 60 |
| 101 | 1 mg/kg | 74 |
| 104 | 1 mg/kg | 81 |
| 109 | 1 mg/kg | 73 |
| 110 | 1 mg/kg | 80 |
| 112 | 1 mg/kg | 75 |
| 114 | 1 mg/kg | 85 |
| 115 | 1 mg/kg | 88 |
|  | 0.1 mg/kg | 37 |
| Desmopressin | 1 mg/kg | 100 |
|  | 10 mg/kg | 100 |

Example 119

Pharmaceutical Composition for Tablet

Tablets containing 100 mg of the compound of Example 1 as the active agent are prepared from the following:

| Compound of Example 1 | 200.0 g |
|---|---|
| Corn starch | 71.0 g |
| Hydroxypropylcellulose | 18.0 g |
| Carboxymethylcellulose calcium | 13.0 g |
| Magnesium stearate | 3.0 g |
| Lactose | 195.0 g |
| Total | 500.0 g |

The materials are blended and then pressed to give 2000 tablets of 250 mg, each containing 100 mg of the compound of Example 5.

The foregoing Examples demonstrate that compounds within the scope of the invention are readily prepared using standard chemical techniques, and that these compounds have the biological properties that would be expected of $V_2$ receptor agonists. In particular, the compounds are potent antidiuretics in an animal model of vasopressin deficiency. Thus it is clear that they may be useful in the treatment of human diseases that are currently treatable with Desmopressin, such as central diabetes insipidus, nocturnal enuresis and nocturia. It has further been suggested that antidiuretics such as Desmopressin may be useful in certain types of urinary incontinence. These arguments would also extend to the compounds of the present invention.

Desmopressin is also used in the treatment of certain coagulation disorders. There is good evidence to suggest that this action is also mediated through the $V_2$ receptor (see for example J E Kaufmann et al., "Vasopressin-induced von Willebrand factor secretion from endothelial cells involves $V_2$ receptors and cAMP", *J. Clin. Invest.* 106, 107–116, 2000; A Bernat et al., "$V_2$ receptor antagonism of DDAVP-induced release of hemostasis factors in conscious dogs", *J. Pharmacol. Exp. Ther.* 282, 597–602, 1997), and hence it would be expected that the compounds of the present invention should be useful pro-coagulants.

The scope of the present invention is further defined in the following claims.

The invention claimed is:

1. A compound according to formula 1, or a pharmaceutically acceptable salt thereof,

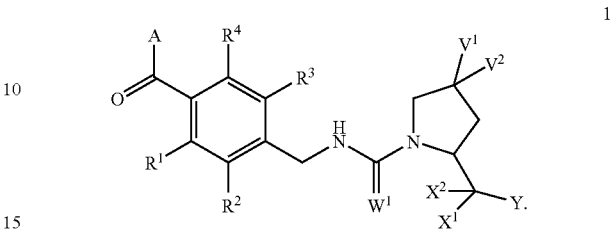

wherein:

A is a benzazepine ring as follows

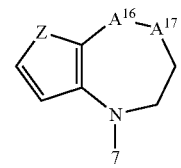

and wherein
$A^{16}$ and $A^{17}$ are both $CH_2$;
Z is —CH=CH—;
$V^1$ and $V^2$ are both H, OMe or F, or one of $V^1$ and $V^2$ is OH, OMe, OBn, OPh, O-acyl, Br, Cl, F, $N_3$, $NH_2$, NHBn or NH-acyl and the other is H, or $V^1$ and $V^2$ together are =O, —S($CH_2$)$_p$S— or —O($CH_2$)$_p$O—;
$W^1$ is either O or S;
$X^1$ and $X^2$ are both H, or together are =O or =S;
Y is $OR^5$ or $NR^6R^7$;
$R^1$, $R^2$, $R^3$, and $R^4$ are independently selected from H, lower alkyl, lower alkyloxy, F, Cl and Br;
$R^5$ is selected from H and lower alkyl;
$R^6$ and $R^7$ are independently selected from H and lower alkyl, or together are —($CH_2$)$_n$—;
n=3, 4, 5 or 6; and
p=2 or 3.

2. A compound according to claim 1, or a pharmaceutically acceptable salt thereof, wherein one of $R^1$ and $R^2$ is Cl or Me and the other is H, and both $R^3$ and $R^4$ are H.

3. A compound according to claim 1, or a pharmaceutically acceptable salt thereof, wherein one of $V^1$ and $V^2$ is OMe or OBn and the other is H.

4. A compound according to claim 1, or a pharmaceutically acceptable salt thereof, wherein $X^1$ and $X^2$ together are =O and Y is $NR^6R^7$.

5. A compound according to claim 1, or a pharmaceutically acceptable salt thereof, which is

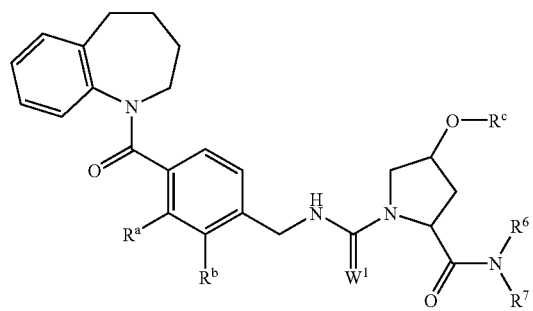

wherein
W¹ is either O or S;
one of $R^a$ and $R^b$ is Cl or methyl and the other is H;
$R^c$ is methyl or benzyl;
$R^6$ and $R^7$ are independently selected from H and lower alkyl, or together are —$(CH_2)_n$—; and
n is 3, 4, 5 or 6.

6. A compound according to claim 1, or a pharmaceutically acceptable salt thereof, which is

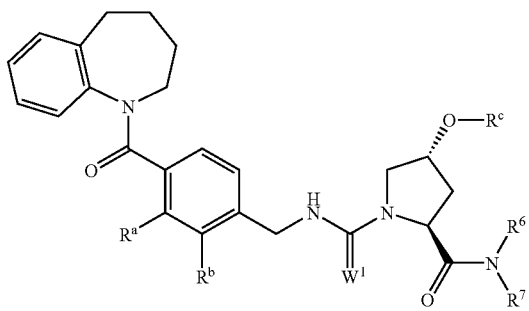

wherein
W¹ is either O or S;
one of $R^a$ and $R^b$ is Cl or methyl and the other is H;
$R^c$ is methyl or benzyl; and
$R^6$ and $R^7$ are independently selected from H and lower alkyl, or together are —$(CH_2)_n$—; and
n is 3, 4, 5 or 6.

7. A compound according to claim 1, or a pharmaceutically acceptable salt thereof, wherein V¹ and V² are both H.

8. A compound according to claim 7, or a pharmaceutically acceptable salt thereof, wherein X¹ and X² together are =O and Y is $NR^6R^7$.

9. A compound according to claim 1, or a pharmaceutically acceptable salt thereof, which is

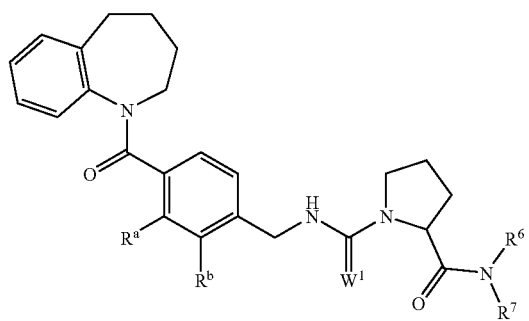

wherein
W¹ is either O or S;
one of $R^a$ and $R^b$ is Cl or methyl and the other is H;
$R^6$ and $R^7$ are independently selected from H and lower alkyl, or together are —$(CH_2)_n$—; and
n is 3, 4, 5, or 6.

10. A compound according to claim 1, or a pharmaceutically acceptable salt thereof, which is

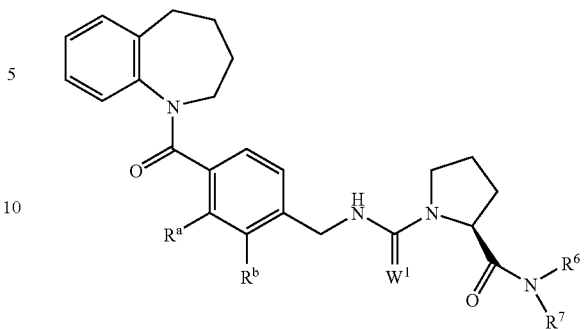

wherein
W¹ is either O or S;
one of $R^a$ and $R^b$ is Cl or methyl and the other is H;
$R^6$ and $R^7$ are independently selected from H and lower alkyl, or together are —$(CH_2)_n$—; and
n is 3, 4, 5 or 6.

11. A compound according to claim 1, which is selected from the group consisting of
1-(2-methyl-4-(2,3,4,5-tetrahydro-1-benzazepin-1-ylcarbonyl)benzylcarbamoyl)-L-proline-N,N-dimethylamide,
(4R)-4-hydroxy-1-(2-methyl-4-(2,3,4,5-tetrahydro-1-benzazepin-1-ylcarbonyl)benzylcarbamoyl)-L-proline-N,N-dimethylamide,
(4R)-1-(3-chloro-4-(2,3,4,5-tetrahydro-1-benzazepin-1-ylcarbonyl)benzylcarbamoyl)-4-methoxy-L-proline-N,N-dimethylamide,
(4R)-1-(2-chloro-4-(2,3,4,5-tetrahydro-1-benzazepin-1-ylcarbonyl)benzylcarbamoyl)-4-methoxy-L-proline-N,N-dimethylamide,
(4R)-4-benzyloxy-1-(2-methyl-4-(2,3,4,5-tetrahydro-1-benzazepin-1-ylcarbonyl)benzylcarbamoyl)-L-proline-N,N-dimethylamide,
(4R)-4-methoxy-1-(2-methyl-4-(2,3,4,5-tetrahydro-1-benzazepin-1-ylcarbonyl)benzylcarbamoyl)-L-proline-N,N-dimethylamide,
(4R)-4-methoxy-1-(3-methyl-4-(2,3,4,5-tetrahydro-1-benzazepin-1-ylcarbonyl)benzylcarbamoyl)-L-proline-N,N-dimethylamide,
or a pharmaceutically acceptable salt thereof.

12. A pharmaceutical composition which contains active agent selected from compounds and pharmaceutically acceptable salts according to claim 1.

13. A method of treatment of a condition selected from the group consisting of nocturnal enuresis, nocturia and central diabetes insipidus, which method comprises the administration to a person in need of such treatment of an effective amount of a composition according to claim 12.

14. A method for the control of urinary incontinence, which method comprises the administration to a person in need of such treatment of an effective amount of a composition according to claim 12.

15. A method of treatment according to claim 14, wherein the treatment results in voiding postponement.

16. A method of treatment of bleeding disorders, which method comprises the administration to a person in need of such treatment of an effective amount of a composition according to claim 12.

* * * * *